(12) United States Patent
Chaoui et al.

(10) Patent No.: US 10,736,697 B2
(45) Date of Patent: Aug. 11, 2020

(54) METHODS, SYSTEMS AND DEVICES FOR PRE-OPERATIVELY PLANNED SHOULDER SURGERY GUIDES AND IMPLANTS

(71) Applicant: IMASCAP SAS, Plouzane (FR)

(72) Inventors: Jean Chaoui, Locmaria-Plouzane (FR); Gilles Walch, Lyons (FR)

(73) Assignee: IMASCAP SAS, Plouzane (FR)

( * ) Notice: Subject to any disclaimer, the term of this patent is extended or adjusted under 35 U.S.C. 154(b) by 443 days.

(21) Appl. No.: 15/028,497

(22) PCT Filed: Oct. 10, 2014

(86) PCT No.: PCT/IB2014/002819
§ 371 (c)(1),
(2) Date: Apr. 11, 2016

(87) PCT Pub. No.: WO2015/052586
PCT Pub. Date: Apr. 16, 2015

(65) Prior Publication Data
US 2016/0296285 A1    Oct. 13, 2016

Related U.S. Application Data

(60) Provisional application No. 61/889,213, filed on Oct. 10, 2013.

(51) Int. Cl.
*A61B 34/10* (2016.01)
*G16H 40/63* (2018.01)
(Continued)

(52) U.S. Cl.
CPC .......... *A61B 34/10* (2016.02); *A61B 17/1739* (2013.01); *A61F 2/4014* (2013.01);
(Continued)

(58) Field of Classification Search
CPC ........ A61B 2034/101; A61B 2034/102; A61B 2034/104; A61B 2034/105; A61B 2034/107; A61B 2034/108
See application file for complete search history.

(56) References Cited

U.S. PATENT DOCUMENTS

| 5,370,692 A | 12/1994 | Fink et al. |
| 2012/0276509 A1* | 11/2012 | Iannotti ................. A61B 34/10 434/267 |

(Continued)

FOREIGN PATENT DOCUMENTS

| WO | 2005016123 A2 | 2/2005 |
| WO | 2011110374 A1 | 9/2011 |

(Continued)

OTHER PUBLICATIONS

International Search Report for PCT/IB2014/002819 dated May 8, 2015.
(Continued)

*Primary Examiner* — Suba Ganesan
(74) *Attorney, Agent, or Firm* — Duane Morris LLP

(57) ABSTRACT

Methods, systems and devices for pre-operatively planned shoulder surgery guides and implants. Pre-operative planning methods for designing a shoulder surgery guide based on considerations of multiple factors affecting the outcome of shoulder surgery. Methods of using surgery guides and implants in patients undergoing shoulder surgery.

9 Claims, 7 Drawing Sheets

(51) Int. Cl.
  *A61B 17/17*  (2006.01)
  *A61F 2/40*  (2006.01)
  *A61B 17/00*  (2006.01)

(52) U.S. Cl.
  CPC .......... *A61F 2/4081* (2013.01); G16H 40/63 (2018.01); *A61B 17/1778* (2016.11); *A61B 2017/00526* (2013.01); *A61B 2034/101* (2016.02); *A61B 2034/108* (2016.02)

(56) References Cited

U.S. PATENT DOCUMENTS

| | | | |
|---|---|---|---|
| 2013/0211531 A1 | 8/2013 | Steines et al. | |
| 2015/0223941 A1* | 8/2015 | Lang ................ | A61B 17/15 623/19.11 |

FOREIGN PATENT DOCUMENTS

| | | |
|---|---|---|
| WO | 2013060851 A1 | 5/2013 |
| WO | 2013062848 A1 | 5/2013 |
| WO | 2013062851 A1 | 5/2013 |
| WO | 2013142998 A1 | 10/2013 |

OTHER PUBLICATIONS

Favre, et al, "Influence of component positioning on impingement in conventional total shoulder arthroplasty," Clinical Biomechanics, Butterworth Scientifics, Nov. 5, 2007, pp. 175-183, vol. 23, No. 2, Guilford, GB.

Gregory, et al, "Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.

Iannotti et al, "Prosthetic positioning in total shoulder arthroplasty," Journal of Shoulder and Elbow Surgery, p. S111-S121, Jan. 1, 2005, vol. 14, No. 1.

Gregory, Thomas, et al., "Accuracy of Glenoid Component Placement in Total Shoulder Arthroplasty and Its Effect on Clinical and Radiological Outcome in a Retrospective, Longitudinal, Monocentric Open Study", PLOS ONE, vol. 8, No. 10 Aug. 1, 2013.

Iannotti, J P, et al., "Prosthetic Positioning in Total Shoulder Arthroplasty", Journal of Shoulder and Elbow Surgery, Mosby, Amsterdam, NL, vol. 14, No. 1 Jan. 1, 2005.

International Search Report and Written Opinion of the International Searching Authority issued for PCT Application PCT/IB2014/002819 dated May 8, 2005.

Favre et al: "Influence of component positioning on impingement in convetional total shoulder arthroplasty", Clinical Biomechanics, Butterworth Scientific Ltd., Guildford, GB, vol. 23, No. 2 Nov. 5, 2007.

Office Action issued in connection with corresponding Canadian Patent Application No. 2,927,086, dated Oct. 16, 2019, 7 pages.

Extended European Search Report issued in connection with corresponding European Patent Application No. 19209711.1; 12 pages, dated Mar. 23, 2020.

* cited by examiner

METHODS, SYSTEMS AND DEVICES FOR PRE-OPERATIVELY PLANNED SHOULDER SURGERY GUIDES AND IMPLANTS

CROSS REFERENCE TO RELATED APPLICATION

This application claims the benefit of U.S. Provisional Patent Application Ser. No. 61/889,213, filed Oct. 10, 2013, the disclosure of which is incorporated herein by reference in its entirety.

TECHNICAL FIELD

The presently disclosed subject matter relates to methods, systems and devices for pre-operatively planned shoulder surgery guides and implants. The presently disclosed subject matter also relates to the use of such surgery guides and implants in patients undergoing shoulder surgery.

BACKGROUND

Shoulder replacement is a common surgical operation that has achieved positive results for many patients. Indeed, approximately 10% of joint replacement procedures globally are related to the shoulder. Many shoulder procedures are performed in a patient where substantially normally bone exists for orientation and fixation of a prosthetic replacement, or resurfacing. In these cases, the need for the shoulder replacement can often times be related mostly to the arthritic condition of the joint, and relative absence of healthy cartilage.

In some patients, however, one or more of the bones of the shoulder are not only arthritic, but have also had previous conditions that have caused bone to wear away. In such cases, there may not be sufficient bone to adequately affix a prosthetic implant to the bone, or the bones may have been worn such that the orientation of a joint replacement cannot be satisfactorily determined to ensure a positive patient outcome.

There are a number of factors that complicate the selection, orientation and affixation of prosthetic implant devices, such as glenoid implants and/or humeral implants. Failure to properly account for each factor can lead to improperly sized, misaligned and/or poorly affixed implants that result in a poor surgical outcome for the patient.

In order to increase the likelihood of successful patient outcomes in patients undergoing shoulder surgery, methods, systems and devices are needed that allow for the full understanding and incorporation of all necessary factors for optimization of shoulder implant selection and placement. Thus, a need remains for methods, systems and devices for pre-operatively planned shoulder surgery guides and implants that achieve desired outcomes.

SUMMARY

The presently disclosed subject matter provides methods, systems and devices for pre-operatively planned shoulder surgery guides and implants. The presently disclosed subject matter also provides uses of such surgery guides and implants in patients undergoing shoulder surgery.

An object of the presently disclosed subject matter having been stated hereinabove, and which is achieved in whole or in part by the presently disclosed subject matter, other objects will become evident as the description proceeds when taken in connection with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which.

DETAILED DESCRIPTION

Figure 1A:
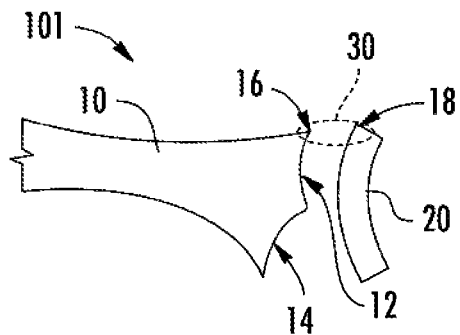
FIG. 1A is a schematic illustration of a step in a pre-operative planning method for designing a shoulder surgery guide where the anterior edge of a glenoid implant is aligned with an anterior edge of a glenoid bone, according to an embodiment of the disclosed subject matter.

Patients requiring shoulder surgery may have one or more of the bones of the shoulder that are not only arthritic, but may also have had previous conditions that have caused bone to wear away. In such cases, there may not be sufficient bone to adequately affix a prosthetic implant to the bone during a routine shoulder surgery. Indeed, the bones may have been worn such that the orientation of a joint replacement cannot be satisfactorily determined to ensure a positive patient outcome.

The glenoid bone can be subject to increased wear due to bone arthritic conditions of the joint, and due to alterations of a normal soft tissue envelope surrounding the joint. In such cases, the orientation of the face of the glenoid portion of the scapula bone may be altered so that the humeral bone is no longer appropriately apposed to the glenoid surface. In the case where the glenoid is severely worn, there can be two or more risks a surgeon must balance in an attempt to improve shoulder function and pain relief.

First, if the optimal orientation of the diseased but treated shoulder is not found and replicated with the prosthesis the patient may experience most operative complications related to subluxation or dislocation of the replaced shoulder joint. This can occur either due to passive inputs to the shoulder (e.g., leaning against it, or lying in bed), or due to active firing of surrounding soft tissue which is not able to be constrained by the replaced joint surfaces.

Additionally, the fixation of a replacement prosthesis, or implant, to the native patient bone can be problematic. Frequently, in order to counteract the risks associated with joint subluxation and dislocation described above, it can be necessary for a surgeon to orient or position the replacement prosthesis or implant in a position better suited to resist imbalanced muscle forces. In such cases, separation forces between the implant and the bone can increase, which in turn can increase the potential for loosening of the joint prosthesis in the bone. Implant loosening can be related to accelerated implant wear, bone erosion, increased tissue inflammation, joint synovitis, and pain.

In patients that have undergone shoulder replacement surgery, range of motion and strength are dependent on shoulder kinematics, which are in turn dependent on a host of factors. Such factor can, for example, include for example implant size, implant position, the design of implant shape, the joint line and soft tissue tension. In some cases it can be difficult to predict optimal implant size and position/orientation using currently available guides and implants. Often times a surgeon finds that there are too many variables to manage at one time. Moreover, the size choices of implants can be limited to the lowest practically functional groups to reduce economic burden to the health care system. Current implant designs and methodologies are inadequate to address these challenges because they are of significant cost, require time to develop, include increased risk of implant failure, and rely on human judgment of potential outcomes post-operatively.

There are many factors that can affect the optimal positioning of shoulder implants during replacement surgery. For example, such factors can include the patient size, relative bone wear, soft tissue strength and condition, six degrees-of-freedom positioning of the glenoid and/or the humeral prosthesis, selected implant size, preoperative patient activity and strength levels, post operative treatment protocols, size and density of patient bone. Additional factors can include patient smoking status, concomitant handicaps and/or patient problems. It can be quite difficult for a surgeon to understand and balance these factors simultaneously. In addition, only a few of these factors are able to be controlled by the surgeon. Finally, each factor does not necessarily have an equally weighted impact on patient outcome. Nevertheless, it is considered that the implant size, position, orientation and bone preparation of the glenoid and the humerus can have a significant impact on the surgical outcomes.

A factor that further complicates, or makes more difficult, a surgeons task of optimally placing a replacement component or implant to counteract these risk is the fact that the condition of the scapula is such that few landmarks exists for the surgeon the comprehend the implant position within the bone. Thus, frequently a surgeon might find that the implant position is not replicating as was envisioned during the surgical intervention.

Others have attempted to improve a surgeon's chance of providing successful patient outcomes by providing operative techniques and tools. What is missing, however, is the ability to fully understand and incorporate multiple factors to optimize the implant selection and placement. Specifically, in some embodiments, the success of the surgery can be highly dependent on both the selection of the matching a prosthesis or prostheses (humeral and/or glenoid), as well as positioning of this prosthesis, as well as the soft tissue status before the surgery. There have been no previous attempts at including these factors in surgical planning and implant design.

Disclosed herein are methods, systems and devices for pre-operatively planned shoulder surgery guides and implants. Methods, systems and devices are provided for the replacement of the shoulder joint, such as the glenohumeral joint, wherein the conditions of the humeral and soft tissue envelop is taken into consideration. More specifically, what is considered is that the shape and position of the glenoid implant is not based solely on what can be seen and measured on the scapula, but can be chosen, designed, planned and placed with incorporation of the same information related to the humerus. After all, the shoulder is a two part joint, i.e. glenoid and humeral head, wherein both parts work in conjunction with one another, and the factors that affect performance of the device can in some embodiments include factors from both sides of the joint.

Appropriate sizing of the prosthesis can be important to successful outcomes, knowing that oversized or "overstuffed" replacement shoulders are more likely to dislocate, loosen, be painful, and/or have decreased range of motion. Replaced joints where the orientation of the prostheses is improper increases the likelihood of implant dislocation and loosening. Additionally, over-reaming, or too much bone removal, either on the glenoid, or the humerus, can be the cause of implant loosening, "under-stuffing" or inappropriate articular surface placement which can increase pain and decrease range of motion.

Provided herein in some embodiments is a glenoid implant designed and manufactured to specifically match the patient anatomy, including optimal humeral and/or glenoid implant size and shape, and taking into account one or more of the following factors: assessment of the humeral implant fit to the humeral bone; relative hardness of the patient bone preoperatively; height and diameter of the humeral head placed on the humeral stem; orientation, or "offset" of the humeral head; and optimal bone removal for preservation of soft tissue insertion and attachment.

Also provided herein are methods, systems and devices for creation of a shoulder surgery guide based on pre-operative planning which takes into consideration a plurality of factors and assessments. In some embodiments, the creation of a shoulder surgery guide based on pre-operative planning can comprise one or more of the following steps, the combination and order of which can vary: aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting the medialization of the glenoid implant by assessing the volumetric amount of bone needed to be removed by reaming, or the minimum total distance of reaming necessary, in order to optimize the bone to implant interface; analyzing the fixation support in the absence of central pegs that penetrate a vault medially; analyzing the joint line, comprising comparing an original joint line and a new joint line, wherein the new joint line is substantially similar to the original joint line; measuring and matching widths of the glenoid implant and the glenoid bone after reaming and aligning inferior/superior axes of the glenoid implant and bone; assessing and adjusting as needed a thickness/height of the glenoid implant; assessing and adjusting as needed a depth of a glenoid fossa; assessing and adjusting as needed a thickness of a graft; determining a diameter of a humeral head; determining a height of the humeral head; determining a size of humeral bone implant from Houndsfield units measured by an imaging technique (e.g. computed tomography (CT) scan); and/or determining a best fit size of implant from a range of sizes, wherein the range of sizes is selected from the group consisting of length of stem, size of humeral stem, diameter of stem, size diameter of head, height of head, and offset of the center spherical head compared to the center of the face of the humeral stem.

In some embodiments, a pre-operative planning method for designing a shoulder surgery guide is provided for designing a guide for the glenoid. Such a method can be separate from a pre-operative planning method for the humerus, or can in some embodiments be done in conjunction with the planning for the humerus, or humeral side of the joint. Such planning steps particular to the glenoid side of the joint can comprise analysis steps such as those depicted in FIGS. 1A-1I.

For example, a pre-operative planning method for the glenoid can comprise a step 101, as depicted in FIG. 1A, where the anterior edge 18 of glenoid implant 20 can be aligned 30 with anterior edge 16 of glenoid 12 of scapula bone 10 of a patient to be treated. In some embodiments, this step, as with other pre-operative analyses disclosed herein, can be accomplished virtually based on images, e.g. CT images or X-ray images, taken from a subject or patient prior to surgery. By aligning anterior edge 18 of glenoid implant 20 with anterior edge 16 of glenoid 12, data and information can be collected that informs the selection of a glenoid implant and/or supports the creation of a shoulder surgery guide device specific to the patient or subject to be treated.

Figure 1B:
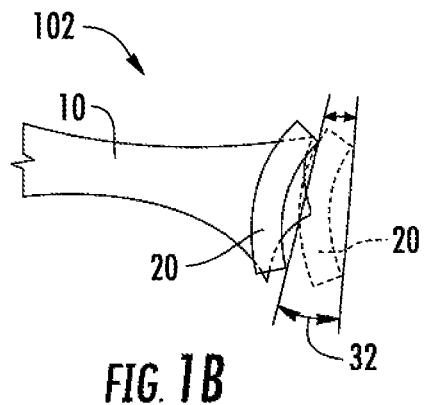
FIG. 1B is a schematic illustration of a step in a pre-operative planning method for designing a shoulder surgery guide where the retroversion of a glenoid implant is adjusted, according to an embodiment of the disclosed subject matter.

In some embodiments, a pre-operative planning method for the glenoid can comprise a step 102, as depicted in FIG. 1B, where the retroversion 32 of glenoid implant 20 is adjusted and/or measured. The retroversion is the placement or degree of posterior rotation of glenoid implant 20 when glenoid 12, including posterior wear 14 (see FIG. 1A), is reamed or otherwise resurfaced to accommodate glenoid implant 20. Such a measurement of retroversion 32 of glenoid implant 20 can be in comparison to the retroversion of the native glenoid in a subject to be treated. In some embodiments, adjusting the retroversion comprises adjusting the retroversion to be about 5 degrees (5°) to about 10 degrees (10°), with a maximum of 10°. In some embodiments, this analysis can be accomplished virtually based on images taken from a subject or patient prior to surgery. By measuring and/or adjusting the retroversion 32 of glenoid implant 20, data and information can be collected that informs the selection of a glenoid implant and/or supports the creation of a shoulder surgery guide device specific to the patient or subject to be treated.

Figure 1C:
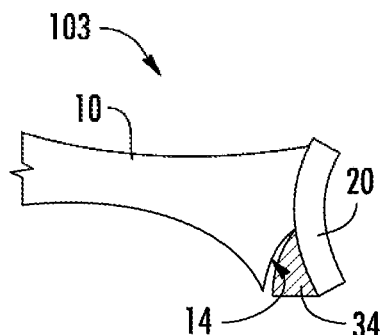
FIG. 1C is a schematic illustration of a step in a pre-operative planning method for designing a shoulder surgery guide where the augmentation of a glenoid implant is adjusted, according to an embodiment of the disclosed subject matter.

In some embodiments, a pre-operative planning method for the glenoid can comprise a step 103, as depicted in FIG. 1C, where a determination can be made as to the necessity of augmentation 34 to support glenoid implant 20. In some embodiments, particularly where glenoid 12 includes posterior wear 14 (or wear at other locations of glenoid 12 not depicted in FIG. 1C), augmentation can be necessary and/or desirable to provide adequate support for the placement and/or attachment of implant 20. Such a step or analysis can in some embodiments comprise adjusting, sizing and/or measuring augmentation 34 needed. In some embodiments, this analysis can be accomplished virtually based on images taken from a subject or patient prior to surgery. By assessing the need for augmentation 34, and/or determining the type and/or size of augmentation 34, data and information can be collected that informs the selection of a glenoid implant and/or supports the creation of a shoulder surgery guide device specific to the patient or subject to be treated.

Figure 1D:
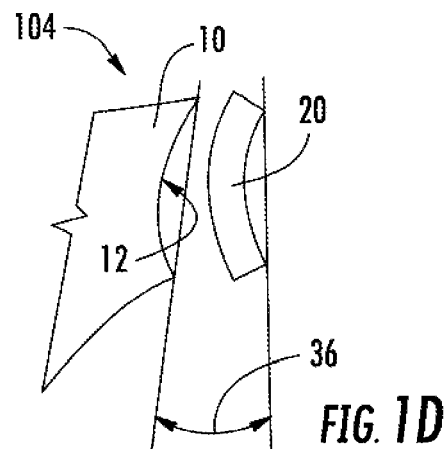
FIG. 1D is a schematic illustration of a step in a pre-operative planning method for designing a shoulder surgery guide where the inferior tilt of a glenoid implant is adjusted, according to an embodiment of the disclosed subject matter.

In some embodiments, a pre-operative planning method for the glenoid can comprise a step 104, as depicted in FIG. 1D, where the inferior tilt 36 of glenoid implant 20 can be measured and/or assessed. Such a measurement of inferior tilt 36 of glenoid implant 20 can be in comparison to the tilt of the native glenoid in a subject to be treated. In some embodiments, this analysis can be accomplished virtually based on images taken from a subject or patient prior to surgery. By assessing the inferior tilt 36 of glenoid implant 20, data and information can be collected that informs the selection of a glenoid implant and/or supports the creation of a shoulder surgery guide device specific to the patient or subject to be treated.

Figure 1E:
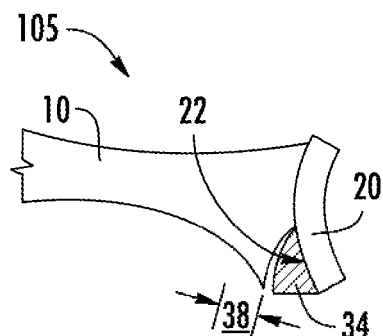
FIG. 1E is a schematic illustration of a step in a pre-operative planning method for designing a shoulder surgery guide where bone support for a glenoid implant is evaluated, according to an embodiment of the disclosed subject matter.

In some embodiments, a pre-operative planning method for the glenoid can comprise a step 105, as depicted in FIG. 1E, where the bone support 38 for glenoid implant 20 can be measured and/or assessed. Such an assessment can in some embodiments comprise characterizing and/or quantifying the amount or degree of bone support 38 for back side 22 of implant 20, taking into consideration posterior wear 14 (see, e.g., FIGS. 1A or 1C; or wear at other locations of glenoid 12 not depicted). In some embodiments, this analysis can be accomplished virtually based on images taken from a subject or patient prior to surgery. By assessing the bone support 38, data and information can be collected that informs the selection of a glenoid implant and/or supports the creation of a shoulder surgery guide device specific to the patient or subject to be treated.

Figure 1F:
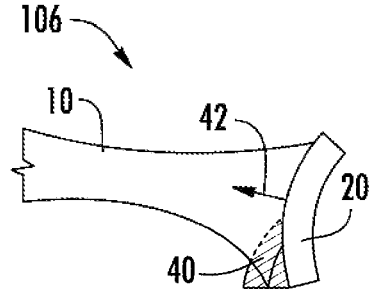
FIG. 1F is a schematic illustration of a step in a pre-operative planning method for designing a shoulder surgery guide where the medialization of a glenoid implant is adjusted by assessing the volumetric amount of bone needed to be removed by reaming, according to an embodiment of the disclosed subject matter.

In some embodiments, a pre-operative planning method for the glenoid can comprise a step 106, as depicted in FIG. 1F, where medialization 42 of glenoid implant 20 can be adjusted and/or characterized by assessing the volumetric amount 40 of bone needed to be removed by reaming. In some embodiments, this analysis can be accomplished virtually based on images taken from a subject or patient prior to surgery. By assessing the bone support 38, data and information can be collected that informs the selection of a glenoid implant and/or supports the creation of a shoulder surgery guide device specific to the patient or subject to be treated.

Figure 1G:
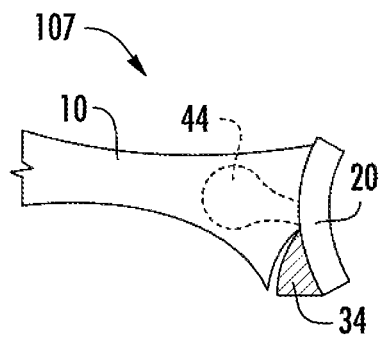
FIG. 1G is a schematic illustration of a step in a pre-operative planning method for designing a shoulder surgery guide where fixation support in the absence of central pegs that penetrate a vault medially is analyzed, according to an embodiment of the disclosed subject matter.

In some embodiments, a pre-operative planning method for the glenoid can comprise a step 107, as depicted in FIG. 1G, where fixation support in the absence of a central peg 44 that penetrates a vault medially of scapula 10 can be analyzed. In some embodiments, it is desirable to identify a location on the glenoid for attachment of a prosthesis using a peg or other fixation component without penetrating the anterior wall of the scapula. In some embodiments, this analysis can be accomplished virtually based on images taken from a subject or patient prior to surgery. By assessing the fixation support, data and information can be collected that informs the selection of a glenoid implant and/or supports the creation of a shoulder surgery guide device specific to the patient or subject to be treated.

Figure 1H:
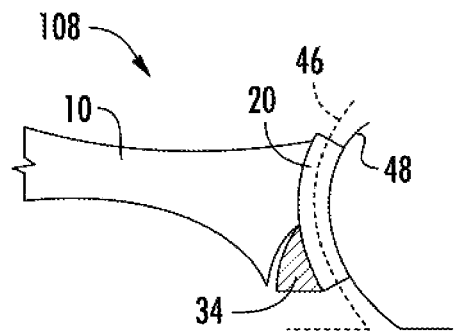
FIG. 1H is a schematic illustration of a step in a pre-operative planning method for designing a shoulder surgery guide where a joint line is analyzed by comparing an original joint line and a new joint line, according to an embodiment of the disclosed subject matter.

In some embodiments, a pre-operative planning method for the glenoid can comprise a step 108, as depicted in FIG. 1H, where a joint line can be analyzed by comparing an original joint line 46 with a new joint line 48 as created when implant 20 is affixed to the glenoid surface of scapula 10. The degree to which the joint line changes or shifts, and/or the change in the angle, can be used in optimizing the implant 20 selection and/or placement. In some embodiments, analyzing the joint line, including comparing the original joint line and the new joint line, can comprise analyzing the humeral head lateralization. Humeral head lateralization can comprise the distance the humeral shaft is moved laterally relative to the scapula after the implants are placed. In some embodiments, this analysis can be accomplished virtually based on images taken from a subject or patient prior to surgery. By assessing the joint line, data and information can be collected that informs the selection of a glenoid implant and/or supports the creation of a shoulder surgery guide device specific to the patient or subject to be treated.

Figure 1I:
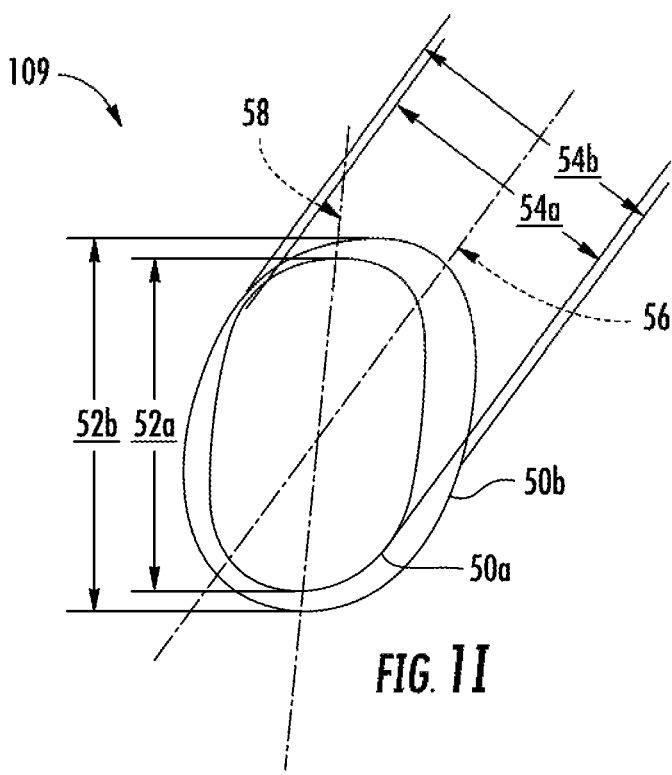
FIG. 1I is a schematic illustration of a step in a preoperative planning method for designing a shoulder surgery guide where widths of the glenoid implant and the glenoid bone are measured and matched after reaming and aligning inferior and superior axes of the glenoid implant and bone, according to an embodiment of the disclosed subject matter.

In some embodiments, a pre-operative planning method for the glenoid can comprise a step 109, as depicted in FIG. 1I, where the widths of the glenoid implant 50*a* and the glenoid bone 50*b* can be measured and matched after reaming and aligning inferior 56 and superior 58 axes of the glenoid implant and bone. Particularly, in some embodiments, a glenoid implant 50*a* height 52*a* and width 54*a* can be measured and aligned with a glenoid bone 50*b* height 52*b* and width 54*b* along inferior 56 and superior 58 axes. In some embodiments, this analysis can be accomplished virtually based on images taken from a subject or patient prior to surgery. By measuring the widths of the glenoid implant 50*a* and the glenoid bone 50*b*, and aligning inferior 56 and superior 58 axes of the glenoid implant and bone, data and information can be collected that informs the selection of a glenoid implant and/or supports the creation of a shoulder surgery guide device specific to the patient or subject to be treated.

Such planning steps particular to the glenoid side of the joint can comprise analysis steps such as those depicted in FIGS. 1A-1I, and can comprise all or some of the steps depicted in FIGS. 1A-1I, and in some aspects can be done in any order desired. Alternatively, in some embodiments analysis steps particular to fixation elements can be performed first followed by analysis steps particular to joint articulation.

In some embodiments, a pre-operative planning method for designing a shoulder surgery guide is provided for designed a guide for the humerus, or humeral bone. Such a method can be separate from a pre-operative planning method for the glenoid (discussed above and depicted in FIGS. 1*a*-1I), or can in some embodiments be done in conjunction with the planning for the glenoid, or glenoid side of the joint. Such planning steps particular to the humerus side of the joint can comprise analysis steps such as those depicted in FIGS. 2A-2D.

Figure 2A:
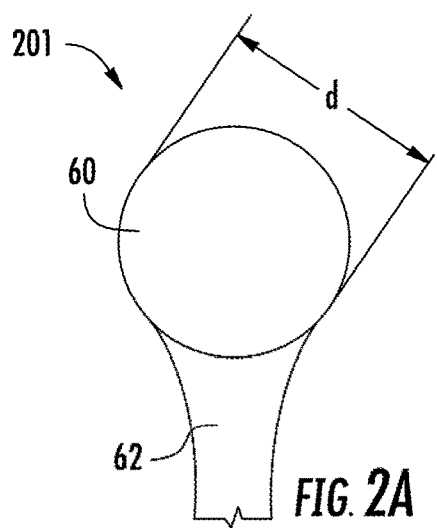
FIG. 2A is a schematic illustration of a step in a preoperative planning method for designing a shoulder surgery guide where the diameter of a humeral head is determined, according to an embodiment of the disclosed subject matter.

For example, a pre-operative planning method for the humerus can comprise a step 201, as depicted in FIG. 2A, where the diameter d of humeral head 60 of humerus 62 can be measured. In some embodiments, this analysis can be accomplished virtually based on images taken from a subject or patient prior to surgery. By measuring diameter d of humeral head 60, data and information can be collected that informs the selection of a humeral head implant and/or supports the creation of a shoulder surgery guide device specific to the patient or subject to be treated.

Figure 2B:
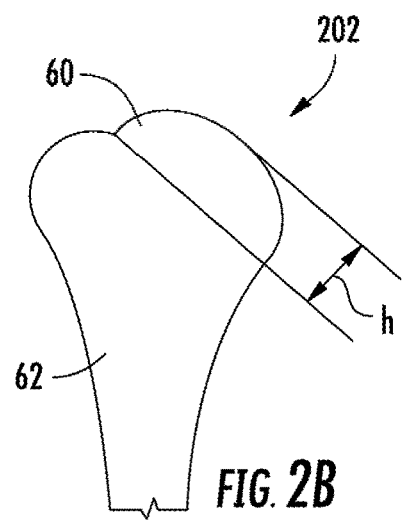
FIG. 2B is a schematic illustration of a step in a preoperative planning method for designing a shoulder surgery guide where the height of a humeral head is determined, according to an embodiment of the disclosed subject matter.

In some embodiments, a pre-operative planning method for the humerus can comprise a step 202, as depicted in FIG. 2B, where the height h of humeral head 60 of humerus 62 can be measured. In some embodiments, this analysis can be accomplished virtually based on images taken from a subject or patient prior to surgery. By measuring height h of humeral head 60, data and information can be collected that informs the selection of a humeral head implant and/or supports the creation of a shoulder surgery guide device specific to the patient or subject to be treated.

Figure 2C:
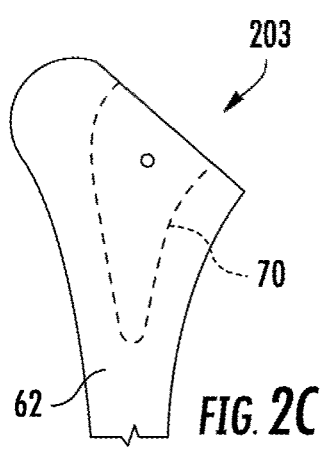
FIG. 2C is a schematic illustration of a step in a preoperative planning method for designing a shoulder surgery guide where the size of a humeral bone implant from Houndsfield units measured by computed tomography scan is determined, according to an embodiment of the disclosed subject matter.

In some embodiments, a pre-operative planning method for the humerus can comprise a step 203, as depicted in FIG. 2C, where the size of a humeral bone implant stem portion 70 can be determined from Houndsfield units (the Hounsfield scale, named after Sir Godfrey Newbold Hounsfield, is a quantitative scale for describing radiodensity) measured by CT scan. In some embodiments, this analysis can be accomplished virtually based on images taken from a subject or patient prior to surgery. By measuring the size of a humeral bone implant, data and information can be collected that informs the selection of a humeral head implant and/or supports the creation of a shoulder surgery guide device specific to the patient or subject to be treated.

Figure 2D:
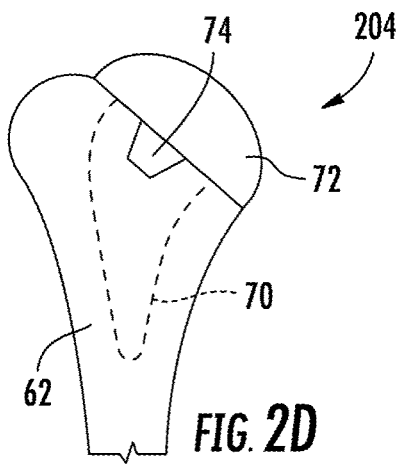
FIG. 2D is a schematic illustration of a step in a preoperative planning method for designing a shoulder surgery guide where a best fit size of implant from a range of sizes is determined, according to an embodiment of the disclosed subject matter.

In some embodiments, a pre-operative planning method for the humerus can comprise a step 204, as depicted in FIG. 2D, where a best fit size of humeral implant 72 from a range of sizes can be determined. In some embodiments, the range of sizes can be selected from the group consisting of length of stem, size of humeral stem, diameter of stem, size diameter of head, height of head, and offset of the center spherical head compared to the center of the face of the humeral stem. In some embodiments, this analysis can be accomplished virtually based on images taken from a subject or patient prior to surgery. By determining the most appropriate size of humeral implant 72, data and information can be collected that informs the selection of a humeral head implant and/or supports the creation of a shoulder surgery guide device specific to the patient or subject to be treated.

Such planning steps particular to the humeral side of the joint can comprise analysis steps such as those depicted in FIGS. 2A-2D, and can comprise all or some of the steps depicted in FIGS. 2A-2D, and in some aspects can be done in any order desired. Alternatively, in some embodiments analysis steps particular to joint articulation can be performed first followed by analysis steps particular to fixation elements.

Figure 3:
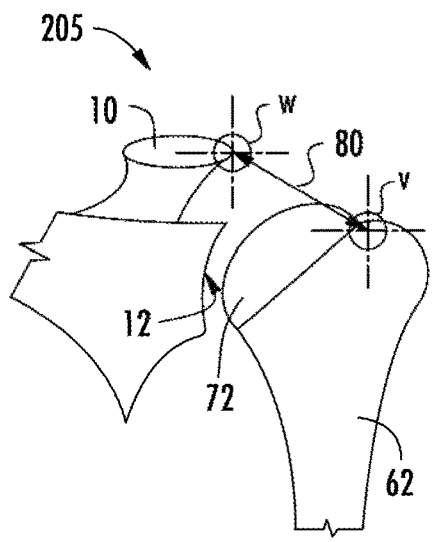
FIG. 3 is a schematic illustration of a step in a preoperative planning method for designing a shoulder surgery guide where vectors are compared in three dimensions to measure the distance of relocation of humeral tuberosity compared to the scapula, according to an embodiment of the disclosed subject matter.

In some embodiments, a pre-operative planning method for designing a shoulder surgery guide can comprise comparing vectors 80 in three dimensions to measure the distance of relocation of humeral tuberosity 72 compared to the scapula 10, as depicted in analysis 205 in FIG. 3. For example, there are 3 rotator cuff tendons that attach to the proximal humerus in the area of the greater tuberosity and the scapula. Such attachment points are depicted as v and w, respectively, in FIG. 3. These tendons control much of the rotation of the humerus about the scapula as well as having a part in elevating the humerus. If the vector resolved from these 3 tendons changes, kinematics and kinetics of the glenohumeral joint (joint comprising the glenoid and humerus) change. For example, changing the direction of vector 80 can change wear patterns and range of motion (ROM) of the implanted device versus the native joint. Additionally, in some embodiments, changing the magnitude of vector 80 by lengthening or increasing it with a joint prosthesis that is too large for the joint can result in decreased ROM, pain, and increased wear of the prosthetic components. Finally, changing the magnitude of vector 80 by decreasing or shortening it with a joint prosthesis that is too small for the joint can result in an unstable joint that may dislocate and can result in suboptimal mechanics for elevating the humerus. In some embodiments, this analysis can be accomplished virtually based on images taken from a subject or patient prior to surgery. By comparing vector 80 in three dimensions to measure the distance of relocation of humeral tuberosity 72 compared to the scapula 10, data and information can be collected that informs the selection of a humeral head implant, glenoid implant, and/or supports the creation of a shoulder surgery guide device specific to the patient or subject to be treated.

Figure 4:
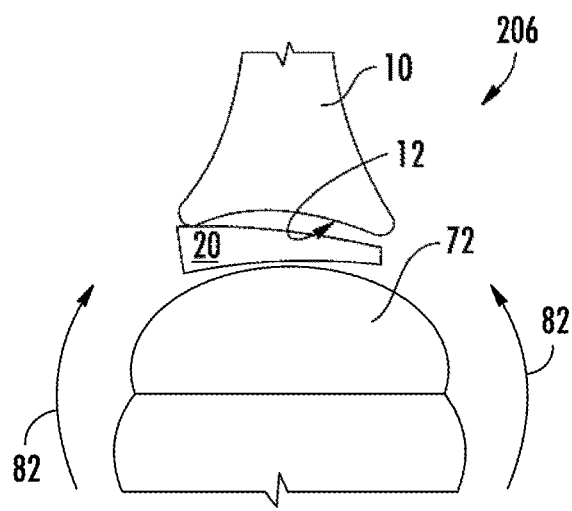
FIG. 4 is a schematic illustration of a step in a preoperative planning method for designing a shoulder surgery guide where range of motion analysis is conducted, including virtually positioning implants through extreme ranges of motion to measure impact locations and compensate for necessary functional range of motion, according to an embodiment of the disclosed subject matter.

In some embodiments, a pre-operative planning method designing a shoulder surgery guide can comprise a step 206, as depicted in FIG. 4, where range of motion (ROM) analysis 82 can be conducted, including virtually positioning implants 20, 72 through extreme ranges of motion to measure impact locations and compensate for necessary functional ROM. In some embodiments, this analysis can be accomplished virtually based on images taken from a subject or patient prior to surgery. By measuring the ROM with respect to glenoid implants 20 and/or humeral implants 72, data and information can be collected that informs the selection of glenoid implant, a humeral head implant and/or supports the creation of a shoulder surgery guide device specific to the patient or subject to be treated.

Figure 5:
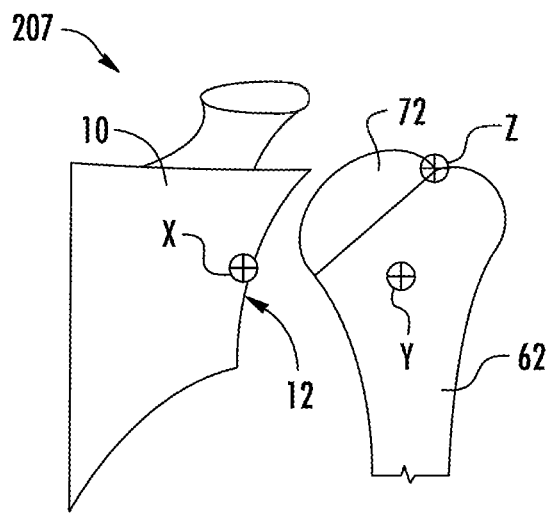
FIG. 5 is a schematic illustration of a step in a preoperative planning method for designing a shoulder surgery guide where soft tissue analysis comprising determining key soft tissue insertion points is conducted, according to an embodiment of the disclosed subject matter.

In some embodiments, a pre-operative planning method designing a shoulder surgery guide can comprise a step 207, as depicted in FIG. 5, where soft tissue, e.g. muscle, analysis is conducted. In some aspects, soft tissue analysis can comprise determining and/or assessing soft tissue insertion points (e.g., X, Y and Z) and analyzing impacts on and/or impacts from use of one or more implants (glenoid and/or humeral). In some embodiments, four rotator cuff muscles and their attachments points can be analyzed. For example, in some aspects analysis can comprise the subscapularis that attaches at an attachment point Y near the lesser tuberosity and at an attachment point X near the anterior glenoid. In some aspects analysis can comprise the supraspinatus that attaches at an attachment point Z near the anterior greater tuberosity and above the scapular spine (shoulder blade; not shown). In some aspects, soft tissue analysis can comprise the infraspinatus that attaches at the greater tuberosity (posterior to supraspinatus) and below the scapular spine (posterior). In some aspects, soft tissue analysis can comprise the teres minor that attaches posterior on the humerus and on the inferior scapular boder. In some embodiments, this analysis can be accomplished virtually based on images taken from a subject or patient prior to surgery. By analyzing the soft tissue around the glenohumeral joint, data and information can be collected that informs the selection of a glenoid implant, a humeral head implant and/or supports the creation of a shoulder surgery guide device specific to the patient or subject to be treated.

In some embodiments, the disclosed pre-operative planning methods can further comprise designing a shoulder surgery guide device based upon parameters collected from the planning methods and analyses. In some embodiments, a designed shoulder surgery guide can be produced, wherein the produced surgery guide is configured in accordance with parameters collected from the planning and analysis specific to the patient to be treated. In some aspects, a guide, and/or a prosthetic implant, can be produced or made using a three dimensional (3D) printing device. In some embodiments, a shoulder surgery guide device produced as disclosed herein can comprise a polymeric or metallic material.

In some embodiments, the disclosed pre-operative planning methods can further comprise identifying a prosthetic shoulder implant, and/or identifying a placement position for the prosthetic shoulder implant. The identification of a prosthetic shoulder implant and placement position takes into consideration at least one of the factors selected from the group consisting of adjustments in glenoid implant size, augmentation depth, augment position, positioning in six degrees of freedom, fixation type, fixation size, reaming depth, reaming diameter, reaming angle, and/or a combination thereof. The above method can further comprise a step of recommending implants and placement positions, with recommended adjustments in humerus stem size, length, head diameter, head height, head offset and rotation (axial). A prosthetic shoulder implant can in some embodiments comprise a glenoid implant.

In some embodiments, the above methods of creating a shoulder surgery guide based on pre-operative planning can further comprise one or more optimization steps. Such optimization steps can comprise the identification of procedural risks based on measurements of one or more of a plurality of factors. Such factors can in some embodiments comprise whether the glenoid face coverage is maximized (e.g. about 0 to about 2 mm), the overhang of the glenoid face is minimized (e.g. about 0 to about 3 mm), and/or the bone removal on the glenoid face is minimized, such as for example less than about 2 mm of depth. Continuing, in some embodiments such optimization factors can comprise whether the glenoid retroversion is less than about 5 degrees to about 10 degrees, the seating of the glenoid implant is greater than about 80%, i.e. about 80% of the back side of the glenoid implant is supported by or touching bone, whether there is minimized penetration of the glenoid cortical wall anteriorily (e.g. about 0 mm to about 3 mm), and/or the depth of any glenoid implant augment feature is as minimal as possible. Still yet, in some embodiments such optimization factors can comprise whether there is less than about 1 mm of difference between the anatomic joint line and the new joint line with implants, there is minimized penetration of the glenoid cortical wall anteriorily, and/or there is maximized bone thickness behind the glenoid, preferably greater than 3 mm. In some embodiments such optimization factors can comprise whether the orientation offset between the native glenoid and implant superior/inferior axis is minimized, preferably less than 5 degrees, the superior or inferior tilt versus native glenoid is minimized, preferably less than 5 degrees, there is less than about 5% to about 10% change in soft tissue length at extreme ranges of motion, there is maximized filing of the humeral metaphysis, in some embodiments greater than about 90% of metaphyseal bone filled based on and identification of metaphyseal bone by use of Houndsfield units, there is an absence of a humeral head overhang compared to the cut, or prepared surface of the humeral bone, there is minimal difference in humeral head diameter between anatomic and implant, in some embodiments less than about 3 mm, there is minimal difference in humeral head height between anatomic and implant, in some embodiments less than about 1 mm, and/or there is greater tuberosity to medial head edge comparison to anatomic, in some embodiments less than about 2 mm. In some embodiments, such procedural risks (any and/or all from the above list) can be determined virtually based on images taken from a subject prior to surgery.

Figure 6:
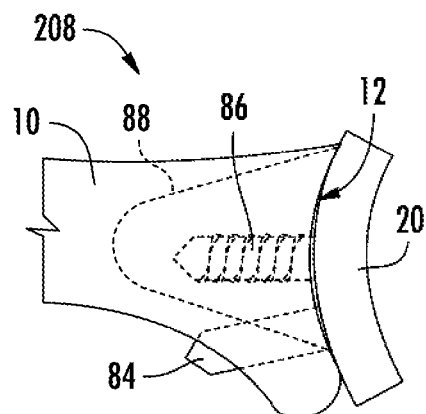
FIG. 6 is a schematic illustration of a step in a preoperative planning method for designing a shoulder surgery guide where penetration of the cortical wall anteriorily of the vault is assessed, according to an embodiment of the disclosed subject matter.

With respect to the above optimization steps that comprise the identification of procedural risks, in some embodiments the penetration of the cortical wall anteriorily of the vault can be assessed, as depicted in FIG. 6. FIG. 6 depicts step 208 of assessing the penetration of the cortical wall anteriorily of the vault 88 by a support structure 84 of glenoid implant 20. In some embodiments, an additional or alternate support structure 86 can be used to affix implant 20 to glenoid 12.

Figure 7:
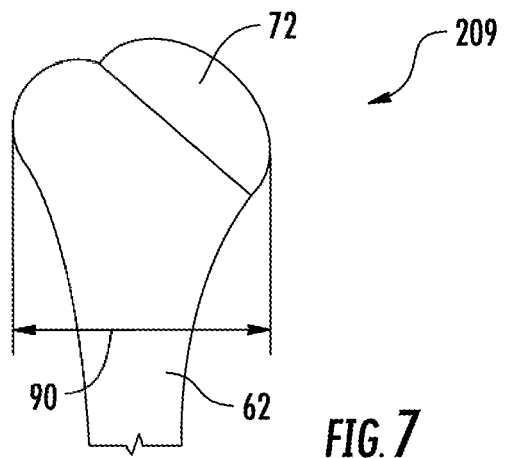
FIG. 7 is a schematic illustration of a step in a preoperative planning method for designing a shoulder surgery guide where the width of the greater tuberosity to medial head edge with an implant is compared to the anatomic width, according to an embodiment of the disclosed subject matter.

Also with respect to the above optimization steps that comprise the identification of procedural risks, in some embodiments the width of the greater tuberosity to medial head edge with an implant can be compared to the anatomic width. For example, in FIG. 7 the width 90 of the greater tuberosity to medial head edge with an implant 72 can be compared to the width of the anatomical humeral head.

In some aspects, the planning methods and analysis steps disclosed herein can be done pre-operatively. That is, they can be done prior to surgery in a virtual or software-based environment. Such virtual simulations can in some embodiments be based on images or scans taken from a subject prior to surgery. Currently available and future imaging techniques, e.g. computed tomography (CT), x-ray imaging, positron emission tomography (PET), ultrasound, etc., can be used to capture images and data to be used in simulation-based analysis and planning to identify suitable prosthetic implants and/or design surgery guides. By using images captured from a subject or patient to be treated, the analysis and results can be specific to the subject or patient and can take into consideration the particularities of that subject's condition.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As such, in some embodiments the disclosed pre-operative planning methods can further comprise providing a computer readable medium having stored thereon executable instructions that when executed by the processor of a computer control the computer to perform one or more of the planning method and/or analysis steps. For example, in some embodiments computer readable medium can have stored thereon executable instructions that when executed by the processor of a computer can control the computer to generate a virtual 3D model of a glenoid guide device reflecting one or more optimized parameters determined during pre-operative planning. Additionally, in some aspects, computer readable medium can have stored thereon executable instructions that when executed by the processor of a computer control the computer to control a 3D printing device in communication with the computer, whereby the 3D printing device can print a glenoid guide device or humeral guide device for use in shoulder replacement surgery in a patient for which pre-operative planning method steps were conducted.

Further, in some aspects of the disclosed methods, systems and devices, a computer readable medium can be provided having stored thereon executable instructions that when executed by a processor of a computer can control the computer to generate a virtual 3D model of a glenoid implant device reflecting one or more optimized parameters determined during pre-operative planning. Thus, in some embodiments a computer readable medium is provided, wherein the computer readable medium has stored thereon executable instructions that when executed by the processor of a computer control the computer to perform one or more of the planning method and/or analysis steps as disclosed herein.

It should be noted that the computers, computing devices, hardware and/or functionality described herein may constitute a special purpose test device. Further, computers, computing devices, hardware and/or functionality described herein can improve the technological field of pre-operative planning for shoulder surgery and can improve generation of virtual modeling systems.

The subject matter described herein for generating 3D models of glenoid and/or humeral implant devices, and/or for modeling and virtually simulating pre-operative shoulder surgery analysis improves the likelihood of a positive outcome from shoulder surgery. It should also be noted that a computing platform, computer, computing device, and/or hardware that implements the subject matter described herein may comprise a special purpose computing device usable to generate 3D models of glenoid and/or humeral implant devices, and/or for modeling and virtually simulating pre-operative shoulder surgery analysis.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments a computer readable medium is provided, having stored thereon executable instructions that when executed by the processor of a computer control the computer to perform steps comprising generating a virtual three dimensional model of a glenoid and/or humeral guide reflecting one or more optimized parameters determined during pre-operative planning based on the above method steps. In some embodiments, a computer readable medium is provided, having stored thereon executable instructions that when executed by the processor of a computer control a 3D printing device in communication with the computer, whereby the 3D printing device prints a glenoid and/or humeral guide for use in shoulder replacement surgery in a patient for which the optimization analysis was conducted.

Figure 8:
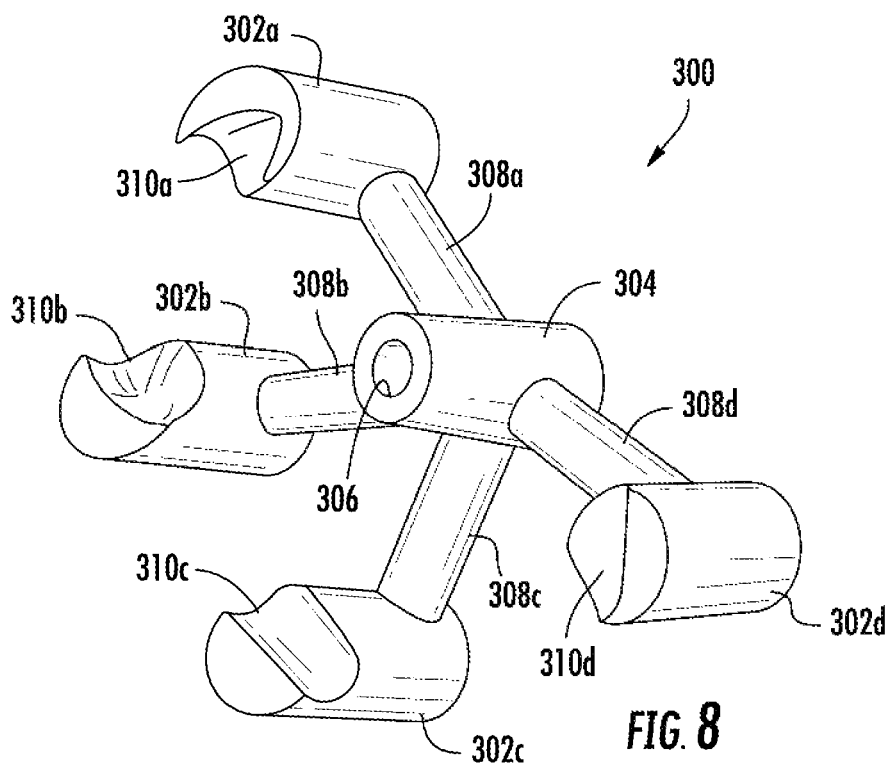
FIGS. 8 and 9 are rear and front perspective views, respectively, of a shoulder surgery guide, according to an embodiment of the disclosed subject matter.
Figure 9:
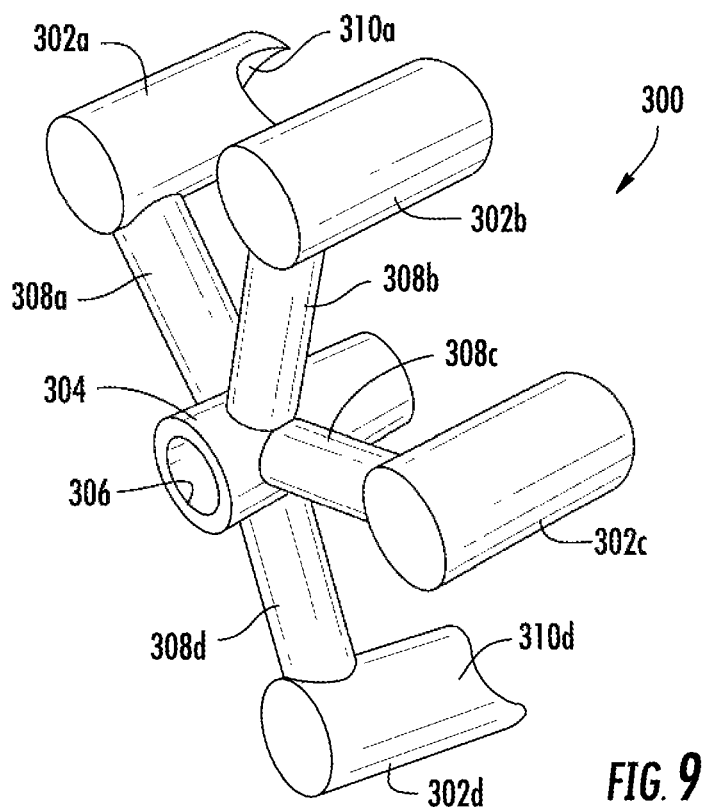
Figure 10:
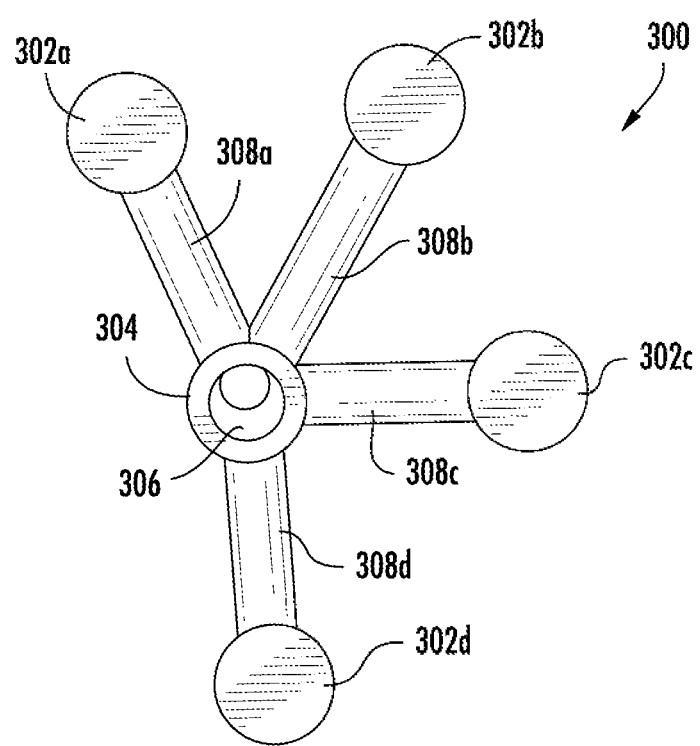
FIG. 10 is a plan view a shoulder surgery guide, according to an embodiment of the disclosed subject matter.
Figure 11:
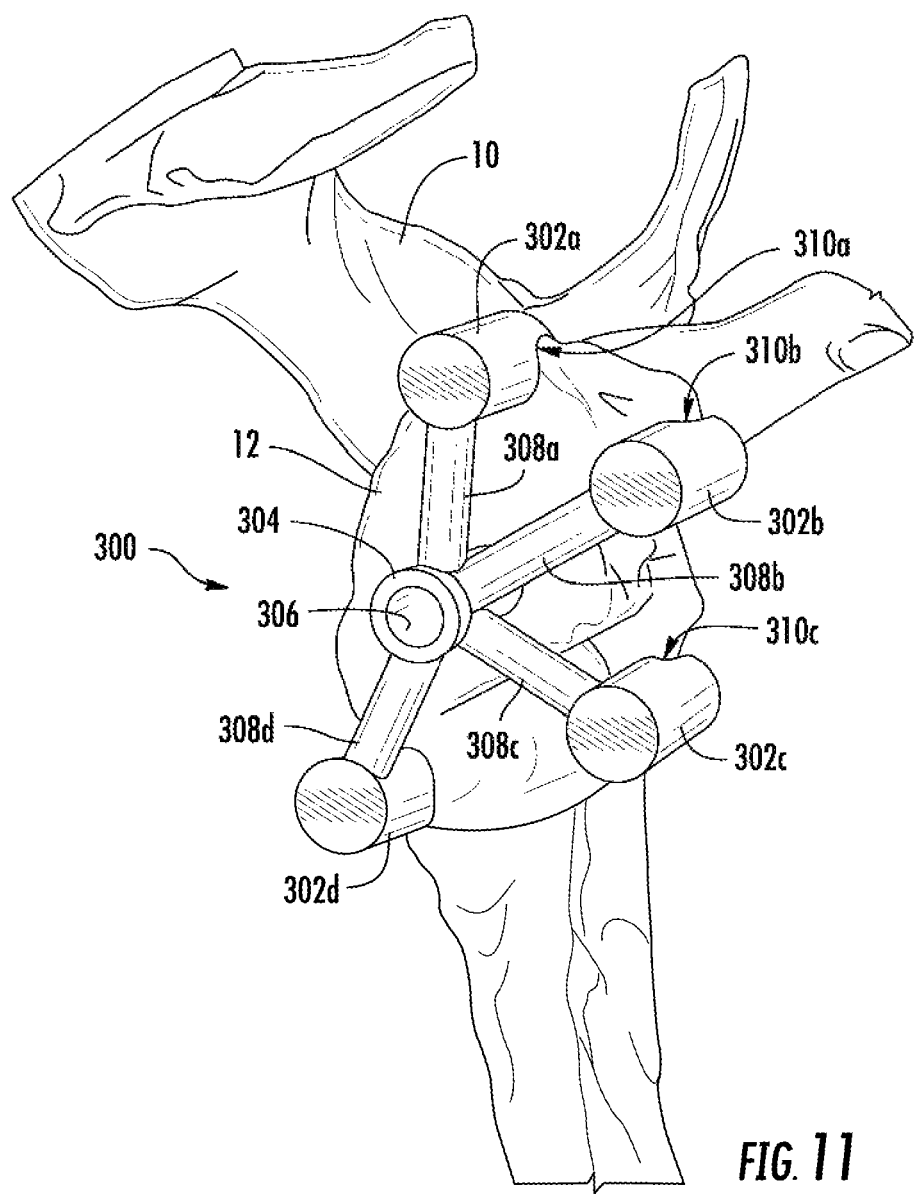
FIG. 11 is a perspective view of a shoulder surgery guide as used during shoulder surgery on a glenoid surface of a scapula, according to an embodiment of the disclosed subject matter.

Based on the pre-operative planning steps and analyses disclosed herein, in some embodiments shoulder surgery guides or guide devices can be designed, simulated and in some instances produced for use in shoulder replacement surgery. Such a surgery guide device is depicted in FIGS. 8-11. FIGS. 8 and 9 are rear and front perspective views, respectively, of a shoulder surgery guide, while FIG. 10 is a plan view of a shoulder surgery guide. As depicted in FIGS. 8-10, shoulder surgery guide 300 can in some embodiments comprise a plurality of peripheral guide structures 302 configured to align with the edge or rim of the glenoid face. In FIGS. 9-11 four peripheral guide structures 302, namely 302a, 302b, 302c, and 302d, are shown, but any number of peripheral guide structures 302, including for example 2, 3, 4, 5, 6, 7, 8, 9 or 10, could be used so long as there are a sufficient number to align and stabilize guide 300 on a glenoid face (see FIG. 11 for a depiction of the guide in use). In some embodiments, peripheral guide structures 302a, 302b, 302c, and 302d can each comprise a corresponding indentation or cupped surface 310a, 310b, 310c, and 310d that can be configured to wrap over the edge of the rim of the glenoid. Cupped surface 310a, 310b, 310c, and 310d can secure and stabilize guide 300 at the desired and predetermined (based on the pre-operative analysis and guide design) location on the glenoid. In some embodiments, some peripheral guide structures may not include a cupped surface, or may include a different shaped structure, as needed to accommodate and align with a given point along the edge of a glenoid. Each peripheral guide structure 302, and corresponding cupped surface 310, can be predetermined and configured based on individual datum points collected during a pre-operative analysis and guide design, as disclosed herein.

Peripheral guide structures 302a, 302b, 302c, and 302d generally extend radially from a hub structure 304, and can be positioned and secured to hub structure 304 by radial arms 308a, 308b, 308c, and 308d. Of course, the number of radial arms 308 will be dictated by, and correspond to, the number of peripheral guide structures 302. The length of radial arms 308 can be determined and configured based on individual datum points collected during a pre-operative analysis and guide design, as disclosed herein, such that each of the peripheral guide structures 302 align with the rim of the glenoid at the desired location.

Hub structure 304 can comprise a central port 306 comprising a cylindrical opening extending through the entire length (see front view FIG. 8, rear view FIG. 9, and plan view FIG. 10) of hub structure 304 and providing an opening through which a pin, drill or boing device can be guided to create an opening, i.e. drill a hole, and/or place a guide pin in the glenoid face. With peripheral guide structures 302a, 302b, 302c, and 302d aligning with the rim or edge of the glenoid, hub structure 304, by virtue of its attachment to each of peripheral guide structures 302a, 302b, 302c, and 302d, can be aligned at the predetermined and desired location on the face of a glenoid. The location of hub structure 304, and particularly central port 306, can be predetermined and configured based on pre-operative analysis such that central port 306 provides a steady and secure guide to the location on the glenoid where a prosthesis or implant is to be attached.

FIG. 11 depicts shoulder surgery guide 300 in use, or aligned with the face of glenoid 12 on scapula 10. Cupped surface 310a, 310b, 310c, and 310d wrap over the edge of the rim of the glenoid 12 such that guide 300 is aligned with and stabilized over glenoid 12. With guide 300 in place on glenoid 12, a pin, drill or boing device can be inserted into central port 306, which can guide the pin, drill or boing device to the precise location on glenoid 12 where a predetermined attachment point is located based on pre-operative analytics.

In some embodiments, a hybrid patient specific implant can be provided, in some embodiments a humeral implant, wherein the hybrid implant can comprise a fixation component and an articular component. The hybrid patient specific implant can comprise a standardized range of fixation components for securing the implant to the humerus. Such fixation component can comprise a stem comprising varying sizes, materials, coatings and surface treatments.

In some embodiments, an intermediate holder can be provided for securing the articular component to the fixation component. Such intermediate holder can vary in size, can comprise standardized materials and coatings, and can comprise a standardized connection between the fixation component, e.g. stem, and holder. Such standardized connection can comprise threads, interlocking components, morse taper connections, snap fit connections (whether using snap rings or not), and the like.

In some aspects, the customized patient specific articular component can comprise a desired articular shape and/or position based on the methods of analysis and optimization disclosed herein. By way of example and not limitation, the shape and position of the articular component can be centered or offset, and can have varying degrees of depth.

In some aspects, the articular component can comprise a desired range of motion blockage. Range of motion tests with virtual pre-operative planning as discussed herein can reveal potential impingement of humeral polyethylene on scapula bone, or humeral tuberosities on acromion. In some aspects, an analysis comparing predicted range of motion based on necessary activities of daily living can be conducted. In some embodiments, a further step can include resolving any conflicts between impingement and activities of daily living needs. Taking these factors into consideration, the articular component shape and placement can then be optimized.

Additionally, in some embodiments, the articular component shape can be adjusted. Such variations, based in some aspects on pre-operative planning as discussed herein, can comprise variations in radial location, depth/magnitude and/or angle.

In some embodiments, methods of treating a patient, and/or surgical methods, are provided wherein one or more of the disclosed methods of analysis and optimization are performed on a patient in need of shoulder or other joint surgery. In some embodiments, methods of treating a patient are provided wherein a disclosed method of analysis and optimization is performed, an optimized guide is designed and created, and one or more glenoid and/or humeral implants are designed, created, and/or selected. In some embodiments, a method of treating a patient can comprise utilizing the pre-operative planning to design and optimize a guide and one or more glenoid and/or humeral implants, and the use of the guide to surgically implant the one or more glenoid and/or humeral prosthetic devices.

In some embodiments, a kit is provided wherein the kit can comprise a set of instructions for performing the disclosed pre-operative planning methods and analyses. Such a kit can further comprise one or more glenoid and/or humeral prosthetic devices, wherein the devices can be customizable or modular in design such that the prosthetic device can be optimized for the patient based on the pre-operative planning analysis. In some embodiments, a kit can further comprise a guide for placing a prosthetic device during shoulder surgery, wherein the guide can be optimized for the patient based on the pre-operative planning analysis. In some embodiments, a kit can further comprise a 3-D printing device for producing a guide and/or one or more glenoid and/or humeral prosthetic devices. In some embodiments, a kit can further comprise a computer-readable medium (software) for use in conducting the pre-operative planning, and designing a guide, glenoid implant and/or humeral implant based on input parameters gathered during the disclosed methods of analysis.

In some embodiments a patient can comprise a mammalian subject. In some embodiments, the patient can be a human subject, including an adult, adolescent or child.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method comprising:
generating a glenoid bone pre-operative image of a subject for shoulder surgery;
performing a virtual pre-operative planning process to design a surgery guide and select at least one implant, wherein the pre-operative planning process generates a plurality of parameters by:
aligning an anterior edge of a virtual glenoid implant with an anterior edge of the glenoid bone pre-operative image;
adjusting a retroversion of the virtual glenoid implant;
adjusting an augmentation of the virtual glenoid implant;
adjusting an inferior tilt of the virtual glenoid implant;
evaluating bone support for the virtual glenoid implant, wherein an amount of a rear surface of the virtual glenoid implant that is supported by or touching bone of the glenoid bone pre-operative image is assessed;
adjusting a medialization of the virtual glenoid implant by assessing the volumetric amount of bone of the glenoid bone pre-operative image-needed to be removed by reaming, or the minimum total distance of reaming necessary, in order to optimize a bone to implant interface;
analyzing fixation support of the virtual glenoid implant in the absence of central pegs that penetrate a vault medially;
analyzing an original joint line and a new joint line created by affixing the virtual glenoid implant to the glenoid bone preoperative image, wherein analyzing the original joint line and the new joint line comprises humeral head lateralization to measure a distance a humeral shaft is moved laterally relative to a scapula in the glenoid bone preoperative image;
measuring and matching widths of the virtual glenoid implant and the glenoid bone pre-operative image after reaming and aligning inferior and superior axes of the virtual glenoid implant and bone of the glenoid bone pre-operative image;
assessing and adjusting as needed a thickness/height of the virtual glenoid implant;
assessing and adjusting as needed a depth of a glenoid fossa of the glenoid bone pre-operative image;
assessing and adjusting as needed a thickness of a virtual graft;
conducting a virtual range of motion analysis to identify impact locations between the virtual glenoid implant and bone of the glenoid bone pre-operative image;
based on the virtual range of motion analysis, assessing and adjusting as needed alignment and positioning of the virtual glenoid implant relative to the glenoid bone pre-operative image;
performing soft tissue analysis to determine soft tissue insertion points and analyze impacts from the use of one or more implants; and
manufacturing the surgery guide based on the plurality of parameters collected from the pre-operative planning process, wherein the surgical guide is configured to prepare a shoulder joint for installation of the at least one implant selected by the virtual pre-operative planning process.

2. The method of claim 1, wherein adjusting the retroversion comprises adjusting the retroversion to be about 5 degrees (5°) to about 10 degrees (10°), with a maximum of 10°.

3. The method of claim 1, wherein manufacturing the surgery guide comprises using a three dimensional printing device.

4. The method of claim 1, wherein the surgery guide comprises a polymeric or metallic material.

5. The method of claim 1, wherein the at least one implant comprises a physical prosthetic shoulder implant, and wherein the pre-operative planning process includes identifying a physical placement position for the physical prosthetic shoulder implant.

6. The method of claim 1, further comprising providing a non-transitory computer readable medium having stored thereon executable instructions that when executed by the processor of a computer control the computer to perform the pre-operative planning process.

7. The method of claim 6, wherein the non-transitory computer readable medium having stored thereon executable instructions that when executed by the processor of the computer control the computer to generate a three dimensional (3D) model of the surgery guide reflecting one or more optimized parameters determined during pre-operative planning.

8. The method of claim 6, wherein the non-transitory computer readable medium having stored thereon executable instructions that when executed by the processor of the computer control the computer to control a 3D printing device in communication with the computer, whereby the 3D printing device prints the surgery guide for use in shoulder replacement surgery in the subject for shoulder surgery.

9. The method of claim 6, wherein the non-transitory computer readable medium having stored thereon executable instructions that when executed by the processor of the computer control the computer to generate a virtual 3D model of an implant reflecting one or more optimized parameters determined during pre-operative planning.

* * * * *